US007767464B2

(12) United States Patent
Kentley et al.

(10) Patent No.: US 7,767,464 B2
(45) Date of Patent: Aug. 3, 2010

(54) METHOD FOR DETECTING COUNTERFEIT PAPER CURRENCY

(75) Inventors: Ronald J. Kentley, Palm Desert, CA (US); Mark Kentley, Palm Desert, CA (US); Jeffrey Fischer, Warminster, PA (US)

(73) Assignee: Clarence J. Venne, LLC, Levittown, PA (US)

( * ) Notice: Subject to any disclaimer, the term of this patent is extended or adjusted under 35 U.S.C. 154(b) by 1185 days.

(21) Appl. No.: 11/293,927

(22) Filed: Dec. 5, 2005

(65) Prior Publication Data

US 2009/0004752 A1 Jan. 1, 2009

Related U.S. Application Data

(60) Provisional application No. 60/704,275, filed on Aug. 1, 2005.

(51) Int. Cl.
*G01N 21/75* (2006.01)
*G01N 33/34* (2006.01)

(52) U.S. Cl. ............................ 436/164; 436/1; 422/61; 162/140; 162/198

(58) Field of Classification Search ..................... 436/1, 436/164; 422/61; 162/140, 198
See application file for complete search history.

(56) References Cited

U.S. PATENT DOCUMENTS

| | | | |
|---|---|---|---|
| D138,621 | S | 6/1944 | White |
| 2,356,399 | A | 8/1944 | Hansen |
| D161,698 | S | 1/1951 | Lorenzen |
| D190,889 | S | 7/1961 | Koenigsberg |
| D194,132 | S | 11/1962 | Countryman |
| D209,715 | S | 12/1967 | Ninesling et al. |
| 3,436,163 | A | 4/1969 | Calabrese et al. |
| D220,248 | S | 3/1971 | Blumenthal |
| D222,336 | S | 10/1971 | Leary |
| D223,438 | S | 4/1972 | Parera |
| 3,885,495 | A | 5/1975 | Funahashi |
| D242,225 | S | 11/1976 | Sinclair |
| D247,697 | S | 4/1978 | Bottcher |
| D250,248 | S | 11/1978 | Grip |
| D255,653 | S | 7/1980 | Lipsz |

(Continued)

FOREIGN PATENT DOCUMENTS

| | | |
|---|---|---|
| KR | 2004-101112 | 12/2004 |

(Continued)

OTHER PUBLICATIONS

International Search Report dated Jun. 28, 2006 for related PCT Application No. PCT/US2006/008637.

(Continued)

*Primary Examiner*—Lyle A Alexander
(74) *Attorney, Agent, or Firm*—Barnes & Thornburg LLP

(57) ABSTRACT

A composition and method of detecting counterfeit paper currency includes applying a test solution to a paper currency having ink printed thereon. If the paper currency is counterfeit, the test solution causes the ink to release from the paper currency. If the paper currency is genuine, the ink will not release from the paper currency. The test solution may be an aqueous-alcohol solution having a chemical thickener, and preferably includes a de-foaming agent, a bactericide/fungicide and a fragrance.

19 Claims, 2 Drawing Sheets

U.S. PATENT DOCUMENTS

| | | | | |
|---|---|---|---|---|
| D255,989 | S | | 7/1980 | Lipsz |
| 4,387,816 | A | | 6/1983 | Weckman |
| 4,447,413 | A | * | 5/1984 | Rippstein, Jr. ........... 514/772.7 |
| D274,697 | S | | 7/1984 | Venne et al. |
| 4,795,156 | A | | 1/1989 | Paulish |
| D300,118 | S | | 3/1989 | Venne et al. |
| 4,863,171 | A | | 9/1989 | Rocheleau |
| 4,869,611 | A | | 9/1989 | Noll |
| D303,926 | S | | 10/1989 | Venne et al. |
| D310,249 | S | | 8/1990 | LaLonde |
| 4,946,053 | A | | 8/1990 | Conrad |
| 5,063,163 | A | | 11/1991 | Carmeli |
| D326,118 | S | | 5/1992 | Black |
| 5,117,993 | A | | 6/1992 | Vesborg |
| D332,050 | S | | 12/1992 | Schmidt |
| D334,399 | S | | 3/1993 | Ziegler |
| 5,222,823 | A | | 6/1993 | Conforti |
| D337,939 | S | | 8/1993 | Smith, Jr. |
| D345,376 | S | | 3/1994 | Underwood, Jr. |
| D352,242 | S | | 11/1994 | Crawford et al. |
| 5,419,592 | A | | 5/1995 | Stuart |
| D367,293 | S | | 2/1996 | Williams |
| D367,943 | S | | 3/1996 | Tien |
| D381,042 | S | | 7/1997 | Rocheleau |
| 5,662,735 | A | * | 9/1997 | Pifferi ....................... 106/31.2 |
| D389,865 | S | | 1/1998 | Venne et al. |
| 5,713,681 | A | | 2/1998 | Venne et al. |
| D396,244 | S | | 7/1998 | Venne et al. |
| D401,270 | S | | 11/1998 | Cockram |
| D403,347 | S | | 12/1998 | Cockram |
| 5,927,880 | A | | 7/1999 | Allison et al. |
| D414,702 | S | | 10/1999 | Bodker et al. |
| D416,199 | S | | 11/1999 | Alguire et al. |
| 6,095,705 | A | | 8/2000 | Philips |
| D432,572 | S | | 10/2000 | Apointe-Oeming |
| D442,633 | S | | 5/2001 | Kalczynski |
| D443,641 | S | | 6/2001 | Mader |
| D445,831 | S | | 7/2001 | Lindner |
| D448,408 | S | | 9/2001 | Calabro |
| 6,294,021 | B1 | | 9/2001 | Platzcke et al. |
| D451,025 | S | | 11/2001 | Meeker et al. |
| 6,330,939 | B1 | | 12/2001 | Pratt |
| D455,782 | S | | 4/2002 | Singh et al. |
| D459,755 | S | | 7/2002 | Calabro et al. |
| D461,502 | S | | 8/2002 | Horie |
| 6,450,719 | B1 | | 9/2002 | Causton et al. |
| D477,668 | S | | 7/2003 | Kipperman et al. |
| 6,786,344 | B2 | | 9/2004 | Kipperman et al. |
| D505,078 | S | | 5/2005 | Fischer et al. |

FOREIGN PATENT DOCUMENTS

| | | |
|---|---|---|
| WO | WO 84/03295 | 8/1984 |
| WO | WO 95/02869 | 1/1995 |

OTHER PUBLICATIONS

Kamioka et al., Chemical Abstracts Key to the World's Chemical Literature, Chemical Abstracts Service, Oct. 20, 1975, vol. 83, No. 16, American Chemical Society, Columbus, Ohio.

* cited by examiner

METHOD FOR DETECTING COUNTERFEIT PAPER CURRENCY

CROSS-REFERENCE TO RELATED APPLICATIONS

This application claims priority from Provisional U.S. App. Ser. No. 60/704,275 filed Aug. 1, 2005, which is incorporated herein by reference in its entirety.

BACKGROUND OF THE INVENTION

The invention is directed to a composition, apparatus and method for detecting counterfeit currency.

It is well known that ever since paper currency was developed and put into use, the governments throughout the world have been concerned with the problem of counterfeiting. As duplicating and printing, and especially color photocopying techniques have advanced over the years, it is more difficult than ever to distinguish between counterfeit and legitimate paper currency. It is obvious that the problem of counterfeiting paper currency is and has been a major concern of many governments, banks, commercial businesses and retail stores around the world.

In response to the challenge of the ever growing concern of counterfeiting, various instruments and detectors have been developed for detecting counterfeit currency. However, it has been discovered that known instruments and detectors are not reliable, or are too expensive to manufacture. In some cases such instruments are too bulky and/or complex in design for practical use.

For example, different compositions have been developed that detect a starch content in counterfeit paper currency. These compositions generally contain iodine, which it is believed, reacts with starch in counterfeit paper currency to form a blue or bluish back stain on the counterfeit paper currency. On the other hand, genuine paper currency either does not contain starch, or its content is chemically untraceable. Therefore, iodine in the composition remains unreacted, or slightly reacted, and either no color change is observed, or a light golden brown color is observed. In many countries throughout the world, however, it is illegal to deface genuine currency by deliberately staining it. In addition, counterfeiters are now bleaching real paper currency and using it to make counterfeit paper currency. Therefore, the above-mentioned compositions for testing the paper will be ineffective.

Prior art currency validators have also been proposed which identify authentic U.S. currency and distinguish between currency of various denominations by measuring the average spacing between the vertical grid lines in the portrait areas of the bills. One such device is disclosed in U.S. Pat. No. 4,349,111, Shah et al. Identification of counterfeit currency based on average grid line spacing is likely to lead to failures to distinguish between currency having relatively small differences, in grid spacing. Another problem with various prior art validators is that they may accept high denomination counterfeit bills as valid lower denomination bills. Moreover, many prior art currency validators require the tested bill be inserted into the validator in a specific orientation (e.g., Federal Reserve seal first). Such devices are subject to user error and may result in authentic bills being rejected merely because of improper orientation.

Experience has shown that there is a large difference in frequency dependent, electrical complex permittivity between genuine and counterfeit bills. Genuine bills have a substantially different complex permittivity which is distinct from the permittivity of counterfeit bills. Expensive, complex devices have been proposed that measure the electrical complex permittivity of paper bills to determine if the bills are genuine or counterfeit.

In recent years, the high quality of copying and printing machines has only served to increase the counterfeiting problem. One of the countermeasures against counterfeiting which has been adopted in many countries is the use of a metal embedded in paper checks or currency notes. However, metal detectors used to distinguish between genuine and counterfeit currency are expensive and too bulky and/or complex in design to be readily used by cashiers.

The present invention is provided to solve the problems discussed above and other problems, and to provide an inexpensive, simple and portable manner in which to detect counterfeit paper currency. A full discussion of the features and advantages of the present invention is deferred to the following detailed description, which proceeds with reference to the accompanying drawings.

SUMMARY OF THE INVENTION

The present invention provides a composition and method of using the composition to determine whether a paper currency is genuine or counterfeit. One embodiment of the present the composition may be comprised of water, a chemical thickener, and a solvent.

In another embodiment of the invention, there is provided an apparatus for detecting counterfeit paper currency having ink printed thereon. The apparatus is comprised of a container having an applicator and an interior cavity. An aqueous-alcohol solution having a chemical thickener (i.e., a test solution) may be located in the interior cavity. The test solution is in liquid communication with the applicator.

In yet another embodiment of the present invention, the composition is applied to an applicator (e.g., a felt pad). The moistened applicator is applied to an area of the paper currency having ink printed thereon. Ink used on genuine paper currency will not release from the paper currency. On the other hand, inks used on counterfeit currency will release from the paper and be transferred to the applicator.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which.

DETAILED DESCRIPTION

Figure 1:
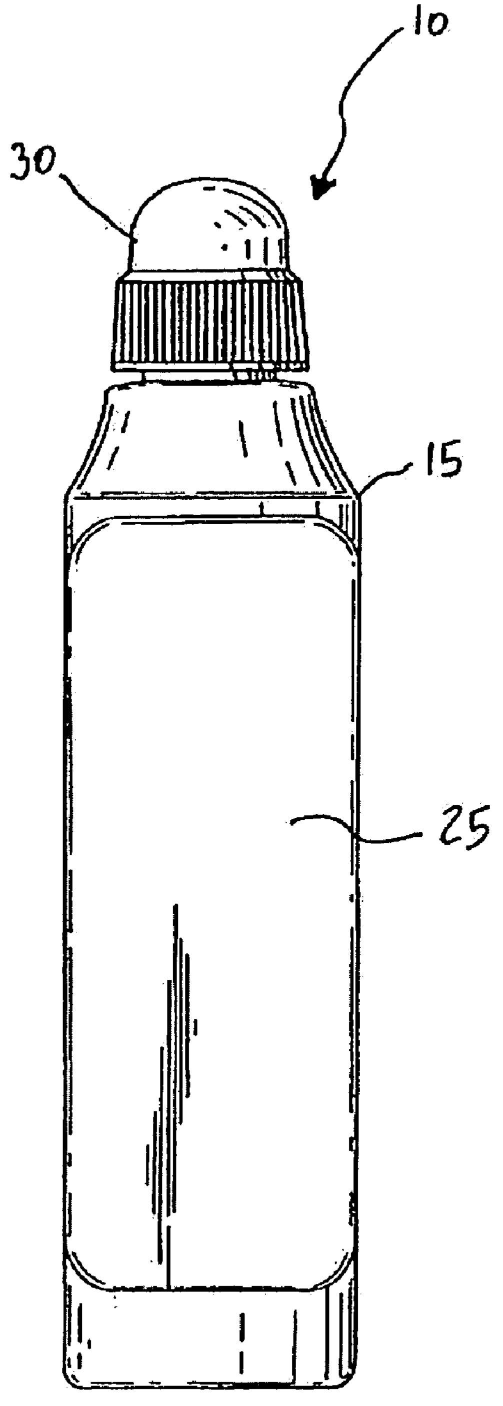
FIG. 1 is a front elevational view of an apparatus containing a test solution according to the present invention.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Although the composition may be any water-based solution, the first embodiment of the composition of the present invention may be obtained by adding a thickener in a range of about 0.1% to 1% of total composition volume to an aqueous (in a range of 89% 90.9% of total composition volume) solvent (in a range of approximately 9%-10% of total composition volume).

EXAMPLE 1

| | |
|---|---|
| Water | 89% by volume |
| Isopropyl alcohol | 10% by volume |
| Xanthan gum | 1% by volume |

The solvent may be a single compound or a mixture of compounds belonging to the same chemical group. For example, the solvent may be an alcohol selected from the following group: isopropyl, methyl, ethyl, propyl, butyl, isobutyl. Or the solvent may be one of the following keytones: acetone, ethylketone, methylethylketone, prophylketone, methylprophylketone. The solvent may also be selected from one of the following polyalcohols: propylene glycol, glycerol, ethylene glycol, or polyethylene glycol. In a preferred embodiment, the solvent is isopropanol in a range of about 0.1% to 10% by total solution volume, available from Ashland Specialty Chemical Co. and other chemical supplies.

Chemical thickeners that may be used in the present invention include gum, sugar, starch or any other commonly known chemical thickener. More particularly, the thickener is a polysaccharide or comprises methylcellulose. In a preferred embodiment, the thickener is xanthan gum and comprises about 0.1% to 1% of the total solution volume. Such a xanthan gum is available from Kelco, a division of Merck & Co., Inc., under the tradename Kelzan S.

In addition to water, solvent and thickener, the composition of the present invention may include: a de-foamer in a range of about 0.1% to 1% of the total solution volume; a bactericide or fungicide in a range of about 0.1% to 1% of the total solution volume; and a fragrance in a range of about 0.1% to 1% of the total solution volume. Examples of a first embodiment of the present invention are illustrated below.

EXAMPLE 2

| | |
|---|---|
| Water | 86% by volume |
| Isopropyl alcohol | 10% by volume |
| Xanthan gum | 1% by volume |
| Defoamer | 1% by volume |
| Bactericide/Fungicide | 1% by volume |
| Fragrance | 1% by volume |

EXAMPLE 3

| | |
|---|---|
| Water | 88% by volume |
| Isopropyl alcohol | 10% by volume |
| Xanthan gum | 0.5% by volume |
| Defoamer | 0.5% by volume |
| Bactericide/Fungicide | 0.5% by volume |
| Fragrance | 0.5% by volume |

-continued

EXAMPLE 4

| | |
|---|---|
| Water | 88% by volume |
| Isopropyl alcohol | 10% by volume |
| Xanthan gum | 0.5% by volume |
| Defoamer | 0.1% by volume |
| Bactericide/Fungicide | 0.1% by volume |
| Fragrance | 0.1% by volume |

The defoamer may also include fatty acids, a blend of fatty acids, various polyglycols (e.g., ethylene glycol, propylene glycol), polyglycol esters (e.g., diethylene glycol distearate, diethylene glycol monostearate, ethylene glycol monostearate, ethylene glycol saturated fatty acid esters, propylene glycol dioleate, propylene glyol monostearate), hydrocarbon oil, and paraffin wax. In a preferred embodiment the defoamer comprises a blend of fatty acids, polyglycols and polyglycol esters in hydrocarbon oil, and is available from Nalco Chemical Company under the product name Nalco 8627 Foam Control Chemical.

Additionally, the preferred bactericide/fungicide is available from Acti-Chem Specialties, Inc. of Trumbull, Conn. under the tradename Acticide LA and the preferred fragrance is a bubble gum fragrance available from Horizon Aromatics of Wilmington, Del. under the tradename Bubble Gum Fragrance 4731, WS. Accordingly, the preferred composition is as follows.

EXAMPLE 5

| | | |
|---|---|---|
| Water | up to 86% | by volume |
| Isopropanol (Isopropanol 99%, Ashland Specialty Chemical Co.) | 10% | by volume |
| Xanthan gum (Kelzan S, Kelco Division of Merck & Co.) | up to 1% | by volume |
| Defoamer (Nalco 8627 Foam Control Chemical, Nalco Chemical Company) | up to 1% | by volume |
| Bactericide/Fungicide (Acticide LA, Acti-Chem Specialties, Inc.) | up to 1% | by volume |
| Fragrance (Bubble Gum Fragrance 4731, WS, Horizon Aromatics) | up to 1% | by volume |

Figure 2:
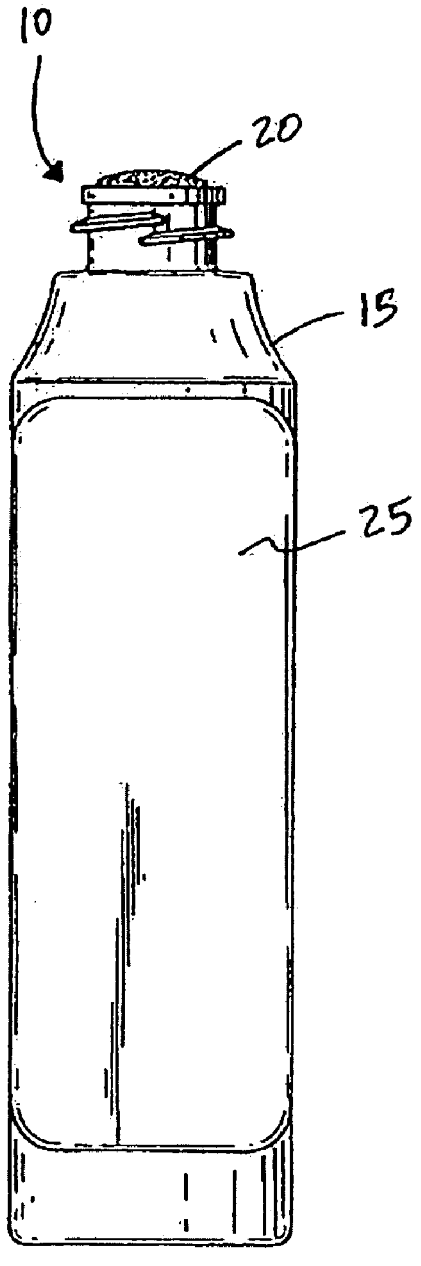
FIG. 2 is a front elevational view of the apparatus of FIG. 1 with the cap removed for convenience of illustration.

With reference to FIGS. 1 and 2, the present invention also provides for an apparatus 10 for detecting counterfeit paper currency having ink printed thereon. The apparatus 10 comprises a container 15 having an applicator 20 and an interior cavity 25. A test solution (e.g., an aqueous-alcohol solution having a chemical thickener as described above) is located within the interior cavity 25 and is in liquid communication with the applicator 20. In a preferred embodiment, the apparatus includes a cap 30, which prevents the applicator 20 from drying out and also prevents the test solution from evaporating. The applicator 20 can be formed from felt, cotton, or even expanded plastic foam. In an alternative embodiment not shown, the applicator 20 is attached to the end of an applicator rod which is housed within the cavity 25. In use, the cap 30 is removed from the applicator 20 and the test solution is applied to the paper currency being tested. It should be understood to those of skill in the art that the container 15 may take the form of a felt tipped marker or similar applicators for liquids. Alternatively, the container 15 can take the form of a solution dropper.

Figure 3:
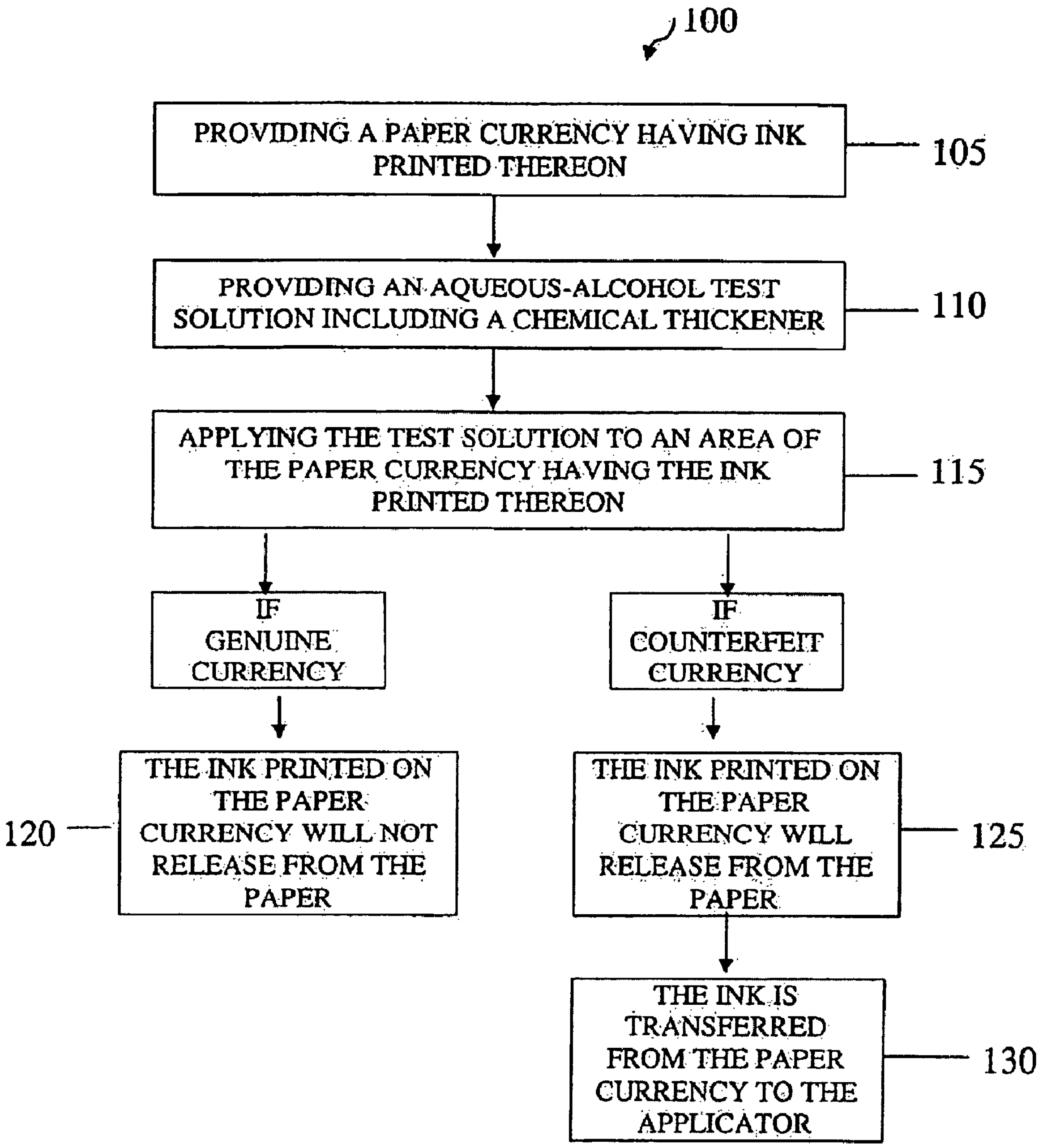
FIG. 3 is a flow chart depicting the steps for a method of detecting counterfeit currency according to the present invention.

Another aspect of the present invention provides a method of detecting counterfeit currency. Referring now to FIG. 3, the method comprises the steps of providing a paper currency having ink printed thereon 100. An aqueous-alcohol test solution including a chemical thickener, as more fully described above, is provided 105. The test solution is applied to an area of the paper currency having the ink printed thereon 110. If the paper currency is counterfeit, the test solution causes the ink to release from the paper currency 125. If the paper currency is genuine, the test solution will not cause the ink to be released from the paper currency 120. In addition to the solutions discussed above, any water-based solution may be used to cause the ink to be released by the counterfeit paper currency. However, the additional chemical components discussed above have been added to enhance the test solution's commercial application and use.

It should be recognized by those having skill in the art that the step of applying the test solution to the paper currency 110 can be carried out in a variety of manners. However, in a preferred embodiment, the test solution is supplied to the applicator 20 (as described above) from the container to moisten the applicator 20. The applicator 20 in turn is rubbed on the area of the paper currency having ink printed thereon. It should be understood that the applicator 20 may be part of an apparatus 10 as described above, or the applicator 20 may simply be a separate pad of felt, a cloth swatch or swab, with the test solution contained in a separate vial or container. The moistened applicator 20 is then rubbed over the area of the paper currency having ink printed thereon. If the paper currency is counterfeit, the ink will release from the paper currency 125. In an even more preferred embodiment, the ink is transferred from the paper currency to the applicator 130. After a paper is tested, the applicator may be wiped clean and used to test the genuineness of another paper currency.

While the specific embodiments have been illustrated and described, numerous modifications come to mind without significantly departing from the spirit of the invention, and the scope of protection is only limited by the scope of the accompanying Claims.

What is claimed is:

1. A method of detecting an ink indicative of counterfeit currency, the method comprising the steps of:

providing a paper currency having ink printed thereon;

providing an aqueous-alcohol test solution including a chemical thickener;

applying the test solution to an area of the paper currency having ink printed thereon; and determining if the application of the test solution caused ink printed on the paper currency to release from the paper currency;

whereby upon application of the test solution to a counterfeit paper currency, the test solution will cause ink printed thereon to be released from the paper currency and for a genuine paper currency the application of the test solution will not cause the ink printed thereon to be released from the paper currency.

2. The method of claim 1 further comprising the step of moistening an applicator with the test solution and then applying the moistened applicator to the area of paper currency having the ink printed thereon.

3. The method of claim 2, wherein the application of the moistened applicator to an area of a counterfeit paper currency having ink printed thereon causes the ink printed thereon to be transferred from the counterfeit paper currency to the moistened applicator and wherein the application of a moistened applicator to an area of a genuine paper currency having ink printed thereon will not cause the ink to be transferred from genuine paper currency to the moistened applicator.

4. The method of claim 1, wherein the test solution comprises water, a chemical thickener, and a solvent.

5. The method of claim 1, wherein the test solution comprises by volume about 0.1% to 10% solvent, about 0.1% to 1% thickener and the remainder water.

6. The method of claim 5, wherein the thickener is a gum.

7. The method of claim 5, wherein the thickener is a sugar.

8. The method of claim 5, wherein the thickener is a starch.

9. The method of claim 5, wherein the thickener is a polysaccharide.

10. The method of claim 5, wherein the thickener comprises methylcellulose.

11. The method of claim 5, wherein the solvent is an alcohol.

12. The method of claim 5, wherein the solvent is an alcohol selected from the group consisting of isopropyl alcohol, isopropanol, methyl alcohol, oxo alcohol, ethyl alcohol, and fatty alcohol.

13. The method of claim 5, wherein the test solution further comprises a defoamer.

14. The method of claim 13, wherein the test solution further comprises by volume about 0.1% to 1% of a defoamer.

15. The method of claim 5, wherein the test solution further comprises a fungicide.

16. The method of claim 15, wherein the test solution further comprises by volume about 0.1% to 1% of a fungicide.

17. A method of detecting an ink indicative of counterfeit currency, the method comprising the steps of:

providing a paper currency having ink printed thereon;

providing a water-based test solution consisting essentially of water, a solvent, a chemical thickener, a defoamer and an antimicrobial;

applying the test solution to an area of the paper currency having the ink printed thereon; and determining if the application of the test solution caused ink printed on the paper currency to release from the paper currency;

whereby upon application of the test solution to a counterfeit paper currency, the test solution will cause the ink printed thereon to be released from the paper currency and for a genuine paper currency the application of the test solution will not cause the ink printed thereon to be released from the paper currency.

18. The method of claim 17 further comprising the step of moistening an applicator with the test solution and then applying the moistened applicator to the area of paper currency having the ink printed thereon.

19. The method of claim 18, wherein the application of the moistened applicator to an area of a counterfeit paper currency having ink printed thereon causes the ink printed thereon to be transferred from the counterfeit paper currency to the moistened applicator and wherein the application of a moistened applicator to an area of a genuine paper currency having ink printed thereon will not cause the ink to be transferred from genuine paper currency to the moistened applicator.

* * * * *